(12) United States Patent
Hein

(10) Patent No.: US 10,809,202 B2
(45) Date of Patent: Oct. 20, 2020

(54) AERATION TESTER

(71) Applicant: Ricardo J. Hein, Acworth, GA (US)

(72) Inventor: Ricardo J. Hein, Acworth, GA (US)

( * ) Notice: Subject to any disclaimer, the term of this patent is extended or adjusted under 35 U.S.C. 154(b) by 0 days.

(21) Appl. No.: 15/985,069

(22) Filed: May 21, 2018

(65) Prior Publication Data

US 2018/0335391 A1 Nov. 22, 2018

Related U.S. Application Data

(60) Provisional application No. 62/509,043, filed on May 19, 2017.

(51) Int. Cl.
| | |
|---|---|
| H04N 5/225 | (2006.01) |
| G01N 21/85 | (2006.01) |
| G01N 33/28 | (2006.01) |
| G01N 1/44 | (2006.01) |
| G01N 15/14 | (2006.01) |
| G01N 35/00 | (2006.01) |
| G01N 15/02 | (2006.01) |
| G01N 21/53 | (2006.01) |
| G01N 1/38 | (2006.01) |
| G01N 35/10 | (2006.01) |
| G01N 15/00 | (2006.01) |
| G01N 21/03 | (2006.01) |

(52) U.S. Cl.
CPC ............... *G01N 21/85* (2013.01); *G01N 1/44* (2013.01); *G01N 15/0227* (2013.01); *G01N 15/1459* (2013.01); *G01N 15/1463* (2013.01); *G01N 21/53* (2013.01); *G01N 33/2888* (2013.01); *G01N 35/00* (2013.01); *G01N 1/38* (2013.01); *G01N 21/0332* (2013.01); *G01N 35/1095* (2013.01); *G01N 2015/0011* (2013.01); *G01N 2015/1493* (2013.01); *G01N 2035/00346* (2013.01); *G01N 2035/00534* (2013.01); *G01N 2201/06153* (2013.01); *G01N 2201/102* (2013.01); *H04N 5/2256* (2013.01)

(58) Field of Classification Search
CPC ...... G01N 21/85; G01N 1/44; G01N 15/0227; G01N 15/1459; G01N 15/1463; G01N 21/53; G01N 33/2888; G01N 35/00
See application file for complete search history.

(56) References Cited

U.S. PATENT DOCUMENTS

| | | | |
|---|---|---|---|
| 4,419,903 A | 12/1983 | Jackson | |
| 5,453,832 A | 9/1995 | Joyce | |
| 6,750,468 B2 | 6/2004 | Malmstrom | |
| 2008/0166037 A1* | 7/2008 | Mandrachia | G01N 15/1463 382/133 |
| 2017/0011506 A1* | 1/2017 | Bojovschi | A61L 15/42 |
| 2017/0030823 A1* | 2/2017 | Wagner | G01N 21/05 |
| 2017/0328924 A1* | 11/2017 | Jones | G01N 15/1463 |

FOREIGN PATENT DOCUMENTS

GB    2001752    2/1979

OTHER PUBLICATIONS

International Search Report and Wrritten Opinion; dated Aug. 8, 2018; 8 pages.

* cited by examiner

*Primary Examiner* — Jonathan R Messmore
(74) *Attorney, Agent, or Firm* — Bennett Mullinax LLC

(57) ABSTRACT

A process and an apparatus for measuring an amount of dissolved air which may be dispersed or entrained in liquids.

7 Claims, 1 Drawing Sheet

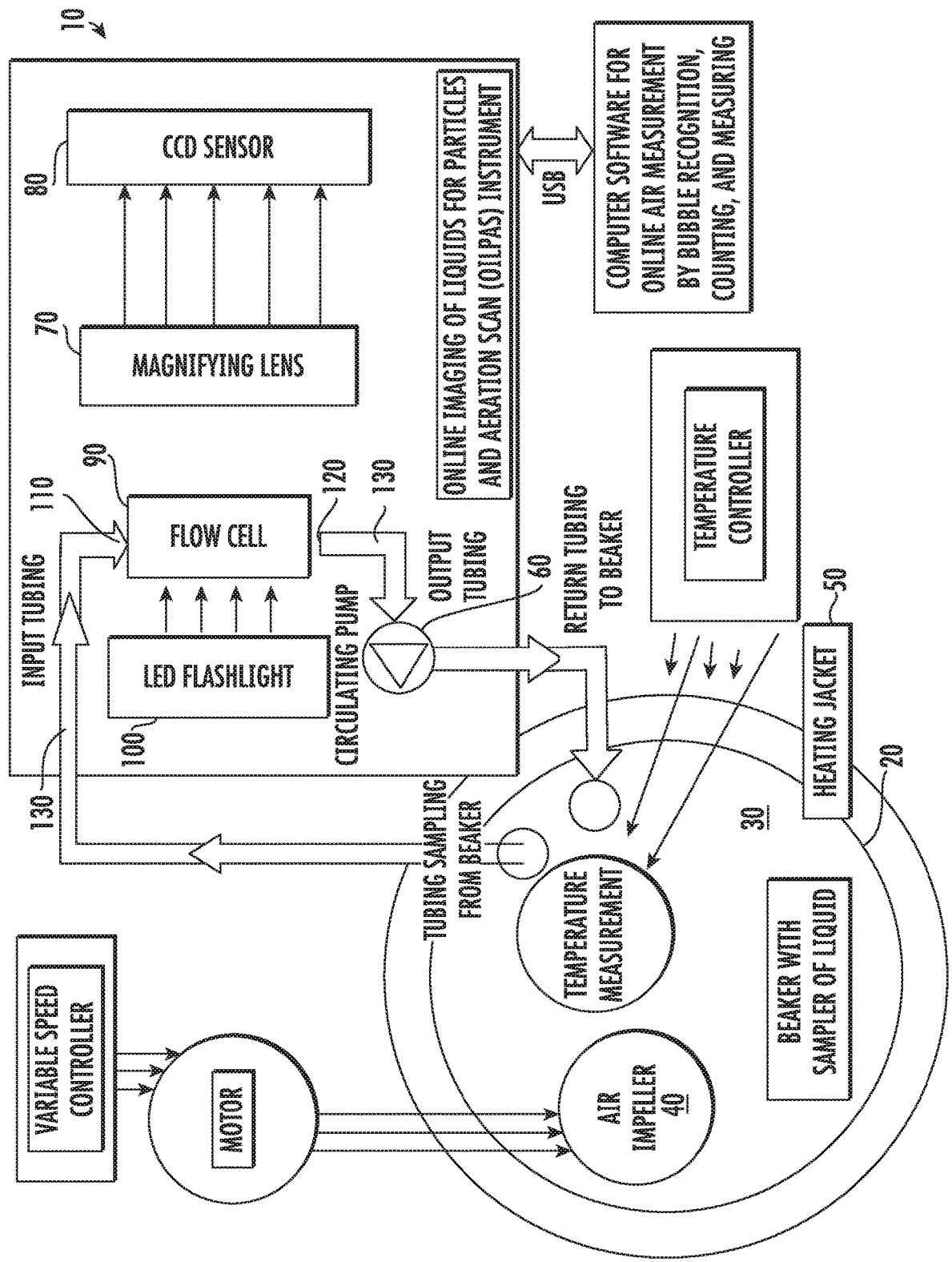

AERATION TESTER

RELATED APPLICATIONS

This application claims the benefit of U.S. Application Ser. No. 62/509,043 filed on May 19, 2017 and which is incorporated herein by reference.

FIELD OF THE INVENTION

This invention is directed towards a process and an apparatus for measuring an amount of air which may be dispersed or entrained in liquids. The apparatus and process is particularly well adapted for use in evaluating characteristics of liquid oils such as motor oil, lubricants, hydraulic liquids, dispersions of water and oil, and other liquids where it is useful to know the air absorption entrainment or dispersion properties beyond their normal limit of solvency of gases at a given pressure.

BACKGROUND OF THE INVENTION

This invention relates to an apparatus and process for measuring oil aeration. Oil aeration is important because many processes that utilize oil for lubrication or hydraulically driven components will entrain additional air as a result of the movement of the oil within a device. The amount of air or other gases within oil can affect the mechanical performances of engines, transmissions, and affect the performance of oils in other applications. For instance, air in oil may cause cavitations and oil compressibility that affects the operation and durability of a mechanical device, Oil oxidation reactions can all have an impact on the performance of oil or other liquid within a mechanical device. Frequently, these oil aeration properties may change over time as the oil or other liquid of interest is subjected to exposure and use within a mechanical device.

There are a number existing test methods for aeration testing. However, such tests are expensive to run and often fail to provide helpful information that can be practically applied to the evaluation of the oil performance itself.

For instance, ASTM D-8047 procedure is designed to test oil aeration resistance in heavy duty diesel engines. The aeration test is expensive to run and provides information on the oil aeration for that engine.

ASTM D-3427 and ASTM D-892 are directed to air release and foaming standards. However, the data generated is not representative of actual oil aeration performance within mechanical components.

ISO 12152 (Flender foaming task) can be used to measure increased volume as a result of aeration but yields inaccurate data with respect to the method of measuring that increasing volume.

Accordingly, there remains room for improvement and variation within the art.

SUMMARY OF THE INVENTION

It is one aspect of at least one of the present embodiments to provide for an apparatus and process that can measure aeration within an oil.

It is a further aspect of at least one embodiment of this invention to provide for an apparatus and a process for measuring the amount of air present in a liquid and which further provides an apparatus and a process for measuring air within a liquid by entraining additional air within the liquid over a range of temperatures.

It is a further aspect of at least one embodiment of the present invention to provide for an apparatus for calculating a gas to liquid ratio comprising: a container for receiving a sample of a liquid, the liquid selected from the group consisting of a lubricating oil, a hydraulic oil, liquid additives, water, water emulsions, aqueous liquids, cleaning product and similar liquids; a temperature regulator for heating or cooling the liquid to a desired testing temperature; a variable speed mixer for mixing the sample with an ambient air source, the variable speed mixer selected from the group consisting of an ultra sonic mixer, a vortex mixer, a static mixer, a rotary blade mixer, a magnetic stir bar, and combinations thereof; a first conduit having a first end in communication with the container and a second end in communication with an input port of a flow cell; a second conduit having a first end in communication with an outlet port of a flow cell and a second end in combination with the container; a light source positioned on a first side of the flow cell; a digital imaging capturing device positioned on a second side of the flow cell; a communication port facilitating the transfer of data from the digital imaging capturing device to a microprocessor the microprocessor controlling a software analytic platform for detecting and characterizing air bubbles within a sample liquid present within the flow cell.

It is a further aspect of at least one embodiment of the present invention to provide for a process for determining a gas to liquid ratio within a liquid comprising the steps of: providing a container for receiving a sample of a liquid; bringing the liquid sample to a desired testing temperature; entraining air into the liquid sample using a mixer; transferring a portion of a sample of the liquid to a flow cell having a transparent window therein; illuminating the portion of the sample within the flow cell with a light source; collecting a visual image of the contents within the flow cell, the collective image including imagery of air bubbles present within the portion of the sample liquid and within the flow cell; analyzing the captured data to determine the physical properties of the air bubbles present within the captured images; using said data to calculate a gas liquid ratio of the sample liquid.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

The FIGURE is a schematic diagram indicating the components an, aeration tester along with the process provided by the various components that are involved in the aeration testing of a liquid such as an oil.

DESCRIPTION OF THE PREFERRED EMBODIMENT

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention.

For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

It is to be understood that the ranges mentioned herein include all ranges located within the prescribed range. As such, all ranges mentioned herein include all sub-ranges included in the mentioned, ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

In describing the various FIGURES herein, the same reference numbers are used throughout to describe the same material, apparatus, or process pathway. To avoid redundancy, detailed descriptions of much of the apparatus once described in relation to a FIGURE is not repeated in the descriptions of subsequent FIGURES, although such apparatus or process is labeled with the same reference numbers.

As best seen in reference to the FIGURE, an apparatus and process for using an apparatus is provided. As seen in reference to the FIGURE, the apparatus and methodology allows for an evaluation of how much air a liquid, such an, oil, can accommodate under simulated conditions. As used herein, the term "air" includes any ambient atmospheric gases that are in proximity to and can be entrained within a liquid being tested. Accordingly, the term "air", when, used with an oil and a internal combustion engine would include any gaseous products in the immediate environment of the oil that might result from the heating of the oil and absorption of any ambient gases that may be in proximity to the oil.

The apparatus set forth in the FIGURE provides for a reservoir for receiving, a sample of a liquid such as an oil. The reservoir can be a beaker or a flask. Once the desired quantity of a liquid/oil is placed within the container, an impeller apparatus is placed within the container and brought into contact with the liquid to be aerated. Depending upon the conditions to be simulated, a variety of different impellers and/or mixers can be used having various shaped blades. The impeller will create a vortex and stirring reaction within the liquid and at a selected speed range will cause the entrainment of ambient air within the liquid. As a general rule, the more rapid the motion of an impeller, such as a rotating blade, the greater amount of air that is entrained within the liquid.

The container can be placed onto a heating pad or within a heat or cooling jacket such that the temperature of the liquid can be maintained at a desired temperature and can be elevated or reduced in a stepwise manner so as to generate comparative data as a function of the temperature of the liquid.

Typically, aeration is desired using a steady agitation at a constant temperature and for a time interval where the aeration saturation level equilibrium has been obtained. Following equilibrium, a sample of the aerated test liquid is removed by a peristaltic pump which removes a sample of the aerated liquid to a test cell. The test cell is adapted for use with optical imaging devices such as a microscope with a camera which can obtain digital images of bubbles within the test cell. Using conventional analytic software, one can quantify the visualized bubble images within the liquid to obtain information on the air ratio percentage within the oil, surface area of bubbles within the oil, relative size of bubbles within the oil. The consistency of the aeration data from the beginning of the test interval to the end of the test interval also provides useful information with respect to the characteristics of the liquid and its tendency to react with and release entrained air.

One form of a suitable test cell can be in the form of a chamber provided between two glass plates where a laminar flow of liquid there between will allow the gas bubbles to be displayed. A light source such as a LED can be used to illuminate the cell with any form of directional light including back lighting that might be beneficial for the particular combination of the liquid and entrained air bubbles. As the images are captured by the optical imaging device, the capturing images can be transferred to a computer for analysis with software that can calculate the number of bubbles, the volume of bubbles based upon radius, and allow the calculation of the resulting gas to liquid ratio. The nature of the test equipment and the ability to use for optical imaging allows for any desired frequency of sampling of liquid within the cell and provides for a basis for determining the resulting gas to liquid ratio and variability of data.

For instance, a consistent range of calculated ratios within a number of samples is indicative that an equilibrium test condition was achieved for the oil and air combination at the test temperature. Additional sampling can be conducted at other temperatures to provide data on gas ratios as temperature changes. In addition, it is also possible to sample and evaluate the gas ratio during heating transition times from one temperature to another that will also simulate working conditions of a liquid in various mechanical conditions.

Additional variations to the light source can be made utilizing polarized light and/or cross polarization filters so as to increase contrast and visualization varying the light source characteristics can be helpful to the extent there may be multiple components within an air stream that can be visualized using different wavelengths of light. This can be useful in terms of making certain that the air bubbles are readily recognized with a unique color. In addition, varying light source can help identify the presence of possible nucleating agents that might be associated with an increased air bubble formation. Nucleating agents can be in the nature of small finds, chemical additives, or other structural particles that will initiate the formation of an air bubble and/or possible provide an upper limit on an air bubble size by producing a larger number of smaller volume bubbles which can affect the performance characteristics of the liquid.

One embodiment of the invention can be seen in the apparatus 10 set forth in the FIGURE and which provides for a container 20 for receiving a sample of a liquid such as an oil. The container 20 can be a beaker or a flask. Once the desired quantity of a liquid/oil 30 is placed within the container, an impeller apparatus 40 is placed within the container and brought into contact with the liquid 30 to be aerated. Depending upon the conditions to be simulated, a variety of different impellers and/or mixers can be used having various shaped blades. The impeller will create a vortex and stirring reaction within the liquid and at a selected speed range will cause the entrainment of ambient air within the liquid. As a general rule, the more rapid the motion of an impeller, such as a rotating blade, the greater amount of air that is entrained within the liquid.

The container 20 can be placed onto a heater 50 such as a heating pad or within a heat or cooling jacket such that the temperature of the liquid can be maintained at a desired temperature and can be elevated or reduced in a stepwise manner so as to generate comparative data as a function of the temperature of the liquid.

Typically, aeration is desired using a steady agitation at a constant temperature and for a time interval where the aeration saturation level equilibrium has been obtained. Following equilibrium, a sample of the aerated test liquid is removed by a peristaltic pump 60 which removes a sample of the aerated liquid to a test cell. The test cell is adapted for use with optical imaging devices such as a microscope or other magnifier 70 with a camera or CCD sensor 80 which can obtain digital images of bubbles within the test cell. Using conventional analytic software, one can quantify the visualized bubble images within the liquid to obtain information on the air ratio percentage within the oil, surface area of bubbles within the oil, and relative size of bubbles within the oil. One suitable software is ImageJ, available from the National Institute of Health in Bethesda, Md. (USA). The consistency of the aeration data from the beginning of the test interval to the end of the test interval also provides useful information with respect to the characteristics of the liquid and its tendency to, react with and release entrained air.

One form of a suitable test cell can be in the form of a flow cell chamber 90 provided between two glass plates where a laminar flow of liquid there between will allow the gas bubbles to be displayed. This allows the retroactive inlet between the liquid and gas bubble to be used to visualize the bubble and conduct measurements of the bubbles' physical properties and size. A light source 100 such as a LED can be used to illuminate the cell with any form of directional light including back lighting that might be beneficial for the particular combination of the liquid and entrained air bubbles. The flow cell 90 has an inlet 110 and an outlet 120 having tubing 130 connecting the flow cell to the container 20. As the images are captured by the CCD sensor 80 optical imaging device, the capturing images can be transferred to a computer for analysis with software that can calculate the number of bubbles, the volume of bubbles based upon radius, and allow the calculation of the resulting gas to liquid ratio. The nature of the test equipment and the ability to use for optical imaging allows for any desired frequency of sampling of liquid within the cell and provides for a basis for determining the resulting gas to liquid ratio and variability of data.

While much of the testing data for liquids can be conducted at ambient pressure, the test equipment does lend itself to using a sealed vessel where pressure can be changed such that variations of temperature and pressure can be evaluated. This can be important in certain operating conditions where the pressure of a liquid may rapidly change during operation or where the pressure conditions under operation may differ from ambient pressure.

The apparatus and process lends itself to an ability to evaluate liquids during transition times of either temperature or pressure or a combination thereof. For instance, the properties of the liquid with respect to gas ratio may vary at significant break points in a non-linear fashion relative to a particular liquid.

While a suitable optical imaging device may utilize a digital camera and a microscope, other devices such as a coriolis apparatus, a Gama ray absorption apparatus, a radio-nuclei tracer apparatus and similar methodologies can be used for determining the gas ratio through the evaluation of bubbles within the liquid.

A further ability of evaluating the gas ratio during variations of pressure temperature is that it can provide accurate information on performance properties of an oil, such as a lubricating oil, where field conditions can change rapidly. For instance, lubricating oils or hydraulic oils can be subject to rapid pressure changes in operation. Accordingly, it now possible evaluate the gas ratio within a liquid during an interval of a rapid pressure change and thereby better characterize the performance characteristics of the oil under more realistic operating conditions.

In addition to using the impeller to directly entrain ambient air and gases into the fluid, for some applications it may be desired to add a supply line that would directly bubble in an appropriate gas mixture in which the impeller thereafter mixes thoroughly within the liquid. For some types of fluid and operating conditions, the addition of a separate air stream into the fluid followed by mixing can be useful for certain applications of maintaining the sample of a liquid at a desired pressure during the steps of entraining air, transferring the sample, and collecting a visual image of the contents.

The performance apparatus and process also lends itself to evaluating not only virgin materials that are introduced into a mechanical environment, but also can be used to evaluate the liquids following a desired interval of time. For instance, the performance of a used lubricating oil from an internal combustion engine can be, analyzed in a virgin, unused, condition as well as used oils that have been operated in the field for a desired number of operating hours. In use, many lubricating oils and hydraulic liquids will acquire particles, fines, chemical contaminants, and various degradation products associated with the normal operation of the liquid within an mechanical environment. It is now possible to measure in real time the properties of these liquids with respect to gas ratio to determine the effects of normal wear and tear on the liquid characteristics. This, in turn, allows a liquid manufacturer to make adjustments to recommended maintenance schedules, the inclusion of various additives to improve performance with respect to gas oil ratios, and to evaluate the effects of product degradation and performance degradation and as a function of age, operating hours, temperature profiles, and other conditions that can affect the physical qualities of the oil and as measured and reflected in gas oil ratios.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it, should be understood that aspects of the various embodiments may be interchanged, both in whole, or in part. Therefore, the spirit and scope of the appended claims should not be limited to the description of the preferred versions contained therein.

That which is claimed:

1. An apparatus for calculating a gas to liquid oil ratio comprising:
 a container for receiving a sample of an oil;
 a temperature regulator for establishing and maintaining the liquid oil sample to a desired testing temperature;
 a variable speed mixer for mixing of the oil sample with an ambient air source, the variable speed mixer selected from the group consisting of an ultra sonic mixer, a vortex mixer, a static mixer, a rotary blade mixer, a magnetic stir bar, and combinations thereof;

a first conduit having a first end in communication with the container and a second end in communication with an input port of a flow cell;

a second conduit having a first end in communication with an outlet, port of a flow cell and a second end in combination with the container;

a light source positioned on a first side of the flow cell;

a digital imaging capturing device positioned on a second side of the flow cell;

a communication port facilitating the transfer of data from the digital imaging capturing device to a microprocessor the microprocessor controlling a software analytic platform for detecting and characterizing air bubbles within a sample oil present within the flow cell;

wherein the container and the flow cell are maintained within a pressurized housing in which the ambient pressure of the container and the flow cell may be regulated.

2. The apparatus according to claim 1 wherein the light source is an LED light source.

3. The apparatus according to claim 1 wherein the light source additionally includes a least one additional light source having a variable wavelength that can be selected from a wavelength constituting UV light to wavelengths constituting infra red light and visible spectrums there between.

4. A process for determining a gas to liquid ratio within an oil comprising the steps of:

providing a container for receiving a sample of an oil;

bringing the oil sample to a desired testing temperature;

entraining air into the oil sample using a mixer;

varying a pressure of the sample oil to provide a first sample pressure oil prior to introducing the sample oil into the flow cell;

transferring a portion of a sample of the oil to a flow cell having a transparent window therein;

varying a pressure of the portion of the sample of the oil thereby providing a second sample pressure oil within the flow cell;

illuminating the portion of the second sample pressure oil within the flow cell with a light source;

collecting a visual image of the contents within the flow cell, the collective image including imagery of air bubbles present within the portion of the second sample pressure oil;

analyzing the captured data to determine the physical properties of the air bubbles present within the captured images;

using said data to calculate a gas liquid ratio of the sample oil.

5. The apparatus according to claim 1 wherein the oil is selected from the group consisting of a lubricating oil, a hydraulic oil, a motor oil, oil containing emulsions and combinations thereof.

6. The process according to claim 4 wherein said steps of entraining air into the oil and transferring a portion of the sample of the oil are conducted within a variable pressure chamber.

7. The process according to claim 4 wherein said step of entraining air includes injecting air directly to the oil supply while using the mixer.

* * * * *